US00PP28221P2

(12) United States Plant Patent
Hansen

(10) Patent No.: US PP28,221 P2
(45) Date of Patent: Jul. 25, 2017

(54) ***BUDDLEIA* PLANT NAMED 'LAVENDER CUPCAKE'**

(50) Latin Name: *Buddleia davidii*
Varietal Denomination: Lavender Cupcake

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 14/999,589

(22) Filed: May 31, 2016

(51) Int. Cl.
*A01H 5/00* (2006.01)

(52) U.S. Cl.
USPC ..... Plt./242

(58) Field of Classification Search
USPC ..... Plt./242
See application file for complete search history.

*Primary Examiner* — Annette Para

(57) ABSTRACT

The new plant *Buddleia* 'Lavender Cupcake' is a short, compact, round-mounded, multi-stemmed, winter-hardy butterfly bush with flowering in a long narrow thyrse with fragrant, light lavender-purple flowers, early season, from mid-summer until frost from soil line to top of plant. Flowers are set off by lanceolate dark green foliage with silvery tomentose undersides.

1 Drawing Sheet

Botanical classification: *Buddleia davidii.*
Variety denomination: 'Lavender Cupcake'.

BACKGROUND OF THE PLANT

The present invention relates to the new and distinct butterfly bush plant of the Scrophuliariaceae family, *Buddleia* 'Lavender Cupcake' hybridized by Hans A. Hansen in the summer of 2010 at a wholesale perennial nursery in Zeeland, Mich., USA. 'Lavender Cupcake' is the result of an ongoing breeding program conducted by the inventor. The goals for this program have been to produce improved, garden-worthy plants for the ornamental plant market. Seeds from the cross of *Buddleia* 'Blue Chip' U.S. Plant Pat. No. 19,991 as the female or seed patent times the male or pollen parent *Buddleia* 'Evil Ways' (not patented) were collected on Sep. 20, 2010. The new plant, originally assigned breeder code H10-193-01, is a single selected seedling from this cross.

*Buddleia* 'Lavender Cupcake' was first asexually propagated from a single select plant in 2012 by stem tip cuttings at the same nursery in Zeeland, Mich. The resultant asexually propagated plants have been found to be stable and true to type in successive generations of asexual reproduction.

No plants of *Buddleia* 'Lavender Cupcake' have been sold, in this country or anywhere in the world, prior to the filing of this application, nor has any disclosure of the new plant been made prior to the filing of this application except that which may have been disclosed within one year of the filing of this application and was either derived directly or indirectly from the inventor.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

The following traits have been repeatedly observed and are determined to be the unique characteristics of *Buddleia* 'Lavender Cupcake'. *Buddleia* 'Lavender Cupcake' is a unique winter-hardy butterfly bush different from all other *Buddleia* cultivars known to the inventor based on the following combined traits:

1. Winter-hardy shrub, with multiple-stemmed, densely branched, short, round-mounded habit.
2. Many-flowered, narrow, long, outward thyrse over a prolonged period, beginning early in mid-summer until frost, from soil line to top of plant, on first-year growth without vernalization.
3. Fragrant, light lavender-purple flowers.
4. Lanceolate serrulate foliage of dark green on top with silvery tomentose undersides.

The nearest comparison plant is *Buddleia* 'Purple Haze' U.S. Plant Pat. No. 24,514, and the new plant is more compact in width and height. Other similar cultivars include *Buddleia* 'Dartmoor' (not patented) which compared to the new plant is shorter and more compact with flowers less broadly branched. Compared to the female parent 'Blue Chip' the new plant is smaller in height and width, more compact in habit and the flower color is light lavender-purple rather than bluish. Compared with 'Evil Ways' (male parent) the new plant has dark green foliage with silver undersides, the flower is not as purple-red colored and the habit is more compact.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
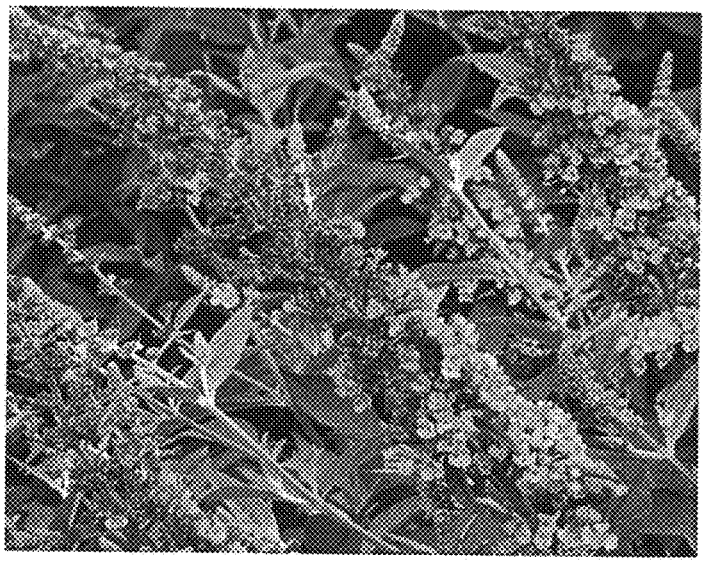
FIG. 1 shows a close-up of the flowers.
Figure 2:
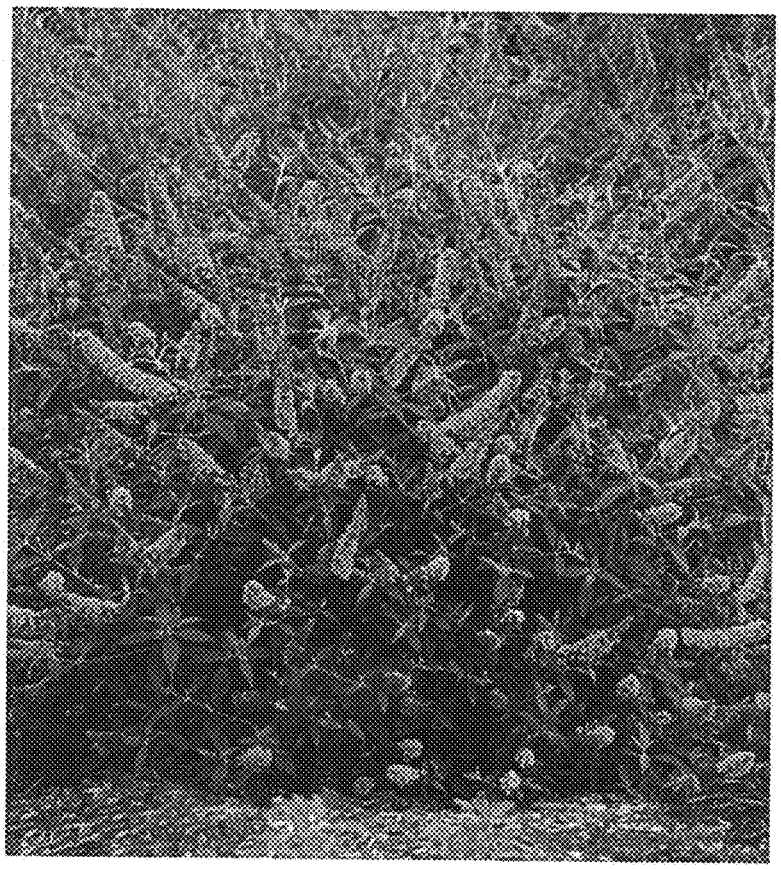
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Lavender Cupcake', has not been observed under all possible environments. The phenotype may vary slightly with different environmental conditions, such as temperature, light, fertility, moisture and maturity levels, but without any change in the genotype. The following observations and size descriptions are of two-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: *Buddleia* 'Blue Chip' as the female or pod parent times 'Evil Ways' as the male or pollen parent.

Propagation:

*Method*.—Softwood cuttings.

*Time to initiate roots from tissue culture*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type.

*Crop time*.—Under normal spring growing conditions 6 to 7 weeks to fill and flower in a four-liter container a 65 mm liner; 8 to 10 weeks to finish and flower in a four-liter container from a 25 mm liner; Plant vigor is very good.

Plant description:

*Plant shape and habit*.—Winter-hardy, semi-woody, well-branched shrub with about 11 thick upright and branched main stems producing a compact rounded mound about 80 cm tall and about 107 cm wide.

*Stem*.—Terete and woody in lower portion with slightly exfoliating bark; younger upper portion puberulent to pulverulent and quadrangular in cross section; strong and flexible; attitude outward in first half of season becoming more drooping toward latter half of season; average about 65 cm tall from soil line to just below terminal flowers, and about 8.0 mm diameter at the base; before distal thyrse about 12 branches per main stem extending at about 60° angle down from main stem.

*Stem color*.—Distal portion just below flowers nearest RHS 138B with blush of nearest RHS N187B where exposed to more intense light; some mid-height stems developing pigment of between RHS 181A and RHS 181B in more intense light; basal woody stem portion blend between RHS 199D and RHS 161D.

*Plant size*.—Unpinched plant with stems flowering to about 80 cm tall; overall plant about 107.0 cm wide.

*Internode*.—About 12 nodes per stem below terminal thyrse, average internode length about 3.0 cm on unpinched plant; upper internodes slightly more elongated than lower internodes; color same as surrounding stem.

Foliage description: Opposite, decussate; serrulate; finely puberulent adaxial and canescent abaxial; elliptic to lanceolate with attenuate base and acute apex; no foliar fragrance detected.

*Leaf blade size*.—Average about 7.0 cm long and about 2.5 cm wide; becoming smaller in distal portion of stem.

*Foliage color*.—Young expanding leaf adaxial side nearest RHS 193B, young expanding abaxial nearest RHS 157A; mature leaves adaxial side nearest RHS 137A and abaxial between RHS 193A and RHS 194B.

*Veins*.—Reticulate; abaxial raised, adaxial slightly impressed; puberulent abaxial and adaxial.

*Vein color*.—Young expanding adaxial center midrib and lateral veins nearest RHS 193B, abaxial young expanding veins nearest RHS 157A; mature adaxial variable midrib nearest RHS 138D lateral veins nearest RHS 137A; abaxial midrib and lateral vein nearest RHS 148D.

*Petioles*.—Puberulent adaxial and abaxial; partially applanate top to bottom; average size about 4.0 mm long and about 2.0 mm wide at the point of attachment to stem.

*Petiole color*.—Nearest RHS 192C abaxial and adaxial.

*Inflorescence description*.—Glomerate thyrse consisting of about 800 self-cleaning salverform flowers; to about 18.0 cm long and about 4.0 cm across; beginning early in mid-July and continuing until frost in Michigan; attitude outward.

*Buds*.—Narrowly spatulate, apex rounded; club glabrous, tube puberulent; one day prior to opening about 8.0 mm long and about 2.0 mm diameter in club, and throat about 1.0 mm diameter in throat and about 6.0 mm long.

*Bud color*.—Between RHS 83A and RHS 83B in club portion; proximal 1.0 mm of tube portion lighter than RHS 145D, proximal region between about 1.0 mm from base and 2.5 mm from base between RHS 145C and RHS 145B, distal two-thirds developing purplish color lighter than RHS N77D.

*Sepals*.—Typically four, proximal two-thirds connate, adpressed to corolla tube; acute apex; glabrous adaxial and puberulent abaxial; margin entire, edentate; fused in about the basal 1.6 mm and split in about the terminal 0.9 mm; forming a corolla about 2.5 mm long and about 1.0 mm across; individually less than about 1.0 mm wide at point of fusion.

*Sepal color*.—Adaxial nearest RHS 137B, abaxial nearest RHS 138B.

*Flowers fragrance*.—Pleasantly and distinctly sweet.

*Lastingness of inflorescence*.—About 10 to 14 days.

*Lastingness of individual flower*.—About 3 to 5 days.

*Flower attitude*.—Upward and outward.

*Petals*.—Typically four; glabrous; fused at base into salverform with typically straight cylindrical tube about 6.0 mm long and 1.0 mm diameter, and a flattened face about 6.0 mm across; petal blade rounded with crenate margin; blade to about 2.5 mm across and about 3.0 mm long from fused face.

*Petal color*.—Adaxial center blended between RHS 25C and RHS 26A in the tube surrounded by a thin irregular band of about 0.5 mm width of lighter than RHS 76D, adaxial face blades nearest RHS 77B; abaxial tube between RHS N163B and RHS N163C, and abaxial petal blades between RHS 77B and RHS 77C.

*Gynoecium*.—Pistil: one; about 3.2 mm long. Style: short, round, glabrous; about 1.6 mm long and less than 0.2 mm diameter; color nearest RHS 144D. Stigma: oblong, minutely puberulent; about 0.2 mm in diameter and about 0.6 mm long; color nearest RHS 141B. Ovary: superior; oblong globose; about 1.0 mm across at base and 1.5 mm tall; distally tapering to style; color between RHS 144A and RHS 144B.

*Androecium*.—Filaments: vestigial or absent; not produced or very short.

*Pedicel*.—Short, puberulent; about 1.5 mm long and about 0.5 mm diameter; color nearest RHS 138A.

*Peduncle*.—Quadrangular, pubescent, flexible and strong; flowering portion to about 28.0 cm long.

*Peduncle color*.—Nearest RHS 138B with blush of nearest RHS N187B where exposed to more intense light.

*Fruit*.—Not observed.

*Seed*.—Not observed.

Disease resistance: Resistance has been noted to deer browsing. Other resistance beyond that of known butterfly bush cultivars has not been observed. The plant grows best with plenty of moisture and adequate drainage, but is able to tolerate some drought when mature. Hardiness at least from USDA zone 5 through 10.

I claim:

1. A new cultivar of winter-hardy butterfly bush *Buddleia* plant named 'Lavender Cupcake' as herein illustrated and described, especially suitable for potted plant culture, landscaping as a specimen or en masse or as cut flower purposes.

* * * * *